(12) United States Patent
Akkerman et al.

(10) Patent No.: US 7,235,787 B2
(45) Date of Patent: Jun. 26, 2007

(54) METHOD AND APPARATUS FOR PERFORMING MEASUREMENTS ON PACKAGING FOR A FLUID PRODUCT

(75) Inventors: Jensen Peter Akkerman, Huizen (NL); Dan Van Der Meer, Delft (NL); Jilles De Wit, Delft (NL); Frederik Nico Endtz, Rotterdam (NL); Arend Van De Stadt, Huizen (NL); Bernardus Cornelis Johannes Landman, Boskoop (NL)

(73) Assignee: Heineken Technical Services B.V. (NL)

( * ) Notice: Subject to any disclaimer, the term of this patent is extended or adjusted under 35 U.S.C. 154(b) by 199 days.

(21) Appl. No.: 10/495,899

(22) PCT Filed: Nov. 18, 2002

(86) PCT No.: PCT/NL02/00749

§ 371 (c)(1),
(2), (4) Date: Jul. 14, 2004

(87) PCT Pub. No.: WO03/042672

PCT Pub. Date: May 22, 2003

(65) Prior Publication Data

US 2005/0040336 A1 Feb. 24, 2005

(30) Foreign Application Priority Data

Nov. 16, 2001 (NL) ..................................... 1019382

(51) Int. Cl.
*G01J 5/02* (2006.01)
*G01N 21/90* (2006.01)

(52) U.S. Cl. ................................. 250/341.8; 250/223 B
(58) Field of Classification Search ............. 250/341.8, 250/223 B
See application file for complete search history.

(56) References Cited

U.S. PATENT DOCUMENTS 3,191,773 A    6/1965    Wyman (Continued)

FOREIGN PATENT DOCUMENTS

DE    197 23 919    12/1998

(Continued)

OTHER PUBLICATIONS

International Search Report dated Jan. 15, 2003.

*Primary Examiner*—Constantine Hannaher
*Assistant Examiner*—Mindy Vu
(74) *Attorney, Agent, or Firm*—Ostrolenk, Faber, Gerb & Soffen, LLP (57) ABSTRACT

The present invention provides a device and a method for performing measurements on packagings, in particular packagings which are at least slightly worn on otherwise to a greater or lesser extent opaque to visible light, which are filled with a liquid product, wherein the packagings are irradiated with radiation in a wavelength range suitable for the packaging with product, and images of at least a part of the content of the packaging are recorded for a predetermined time by image recording means, wherein the obtained image information is analysed for information indicating the presence of undesired particles, and a part of the radiation has a frequency falling within the infrared range.

19 Claims, 5 Drawing Sheets

U.S. PATENT DOCUMENTS

| | | | |
|---|---|---|---|
| 4,087,184 A | | 5/1978 | Knapp et al. |
| 4,672,200 A | * | 6/1987 | Claypool et al. ............ 356/632 |
| 5,442,446 A | * | 8/1995 | Gerber et al. ................ 356/428 |
| 5,864,395 A | | 1/1999 | Laurberg |
| 6,275,603 B1 | * | 8/2001 | Cronshaw et al. ........... 382/142 |

FOREIGN PATENT DOCUMENTS

| | | |
|---|---|---|
| JP | 2001 116700 | 4/2001 |
| WO | WO 97 14956 | 4/1997 |
| WO | WO 00 77499 | 12/2000 |

* cited by examiner

METHOD AND APPARATUS FOR PERFORMING MEASUREMENTS ON PACKAGING FOR A FLUID PRODUCT

BACKGROUND OF THE INVENTION

The present invention relates to a method and an apparatus for performing measurements on packagings for a liquid product. Such apparatus have been developed in order to detect the presence of undesired particles such as glass particles in a liquid product. This is important since the presence of such undesired particles can cause damage to the health of end users and can cause financial loss or commercial damage to the suppliers or manufacturers of such liquid products.

The international patent application WO 97/14956 describes a method and apparatus wherein a detection apparatus is described for detecting glass particles in glass bottles filled with beer. The content of this text is deemed interpolated herein by way of reference. In this apparatus beer bottles are rotated about their longitudinal axis, whereafter the beer bottles are stopped abruptly, i.e. decelerated with force. Shortly hereafter the bottle is illuminated with visible light and image recordings are made of the bottle. On the basis of these images a computer determines whether glass particles are present in the bottle.

SUMMARY OF THE INVENTION

In order to improve this apparatus and method, the present invention provides a method for performing measurements on packagings, in particular packagings which are at least slightly worn or otherwise to a greater or lesser extent opaque to visible light, which are filled with a liquid product, wherein the packagings are irradiated with radiation in a wavelength range suitable for the packaging with product and images of at least a part of the content of the packaging are recorded for a predetermined time by image recording means, wherein the obtained image information is analysed for information indicating the presence of undesired particles, and a part of the radiation has a frequency falling within the infrared range.

At least a part of the radiation preferably has a frequency falling within the infrared range. A number of advantages are achieved by making use of radiation in the infrared range. One advantage that is achieved is that bottles which are not properly transparent can also be processed, such as bottles damaged by so-called "scuffing", bottles of non-homogeneous glass such as the known Coca-Cola™ bottles, bottles with a dark-coloured liquid product, relatively thick-walled bottles, bottles with a product in which for instance yeast or fruit particles are mixed, or for instance decorated or printed bottles or bottles packed by means of a "sleeve". Coloured, for instance blue bottles, for instance for mixed drinks, can also be checked better using infrared radiation, since the radiation is less sensitive to the transmission coefficient of the glass. The stated problems with visible light are avoided as much as possible with infrared radiation. A further advantage is that a lower radiation generating power is required due to the higher energy level of infrared radiation. The mounting bracket of the radiation sources, such as LEDs, can hereby for instance take a smaller form. This has the advantage that, when for instance the radiation sources are applied in a carrousel system to be further described hereinbelow, the total diameter of the carrousel system can become smaller because the individual light sources can take a smaller form. It is also possible to apply radiation sources with different wavelengths, since fewer radiation sources of the same wavelength are required. Two or more different wavelengths can hereby be applied in mounting brackets of the already known format. An advantage hereof is that a specific mix of frequencies can for instance be used for a specific bottle-product combination.

In a further embodiment a distinction is made between information relating to particles which normally form part of the product and information relating to the undesired particles. For instance in the above mentioned fruit juices or beer with secondary fermentation in the bottle, the products comprise natural particles such as fruit pulp or yeast particles in addition to possibly undesirable particles. The application of the method according to this embodiment makes a distinction between these desirable and undesirable particles. It hereby becomes possible that even these products, which are complex for detection of undesired particles, can still be safely supplied.

A further aspect of the present invention relates to an apparatus for performing measurements on full packagings of a liquid product, comprising:

rotation means for rotating the packaging on its own axis for setting the packaging with content into a rotating movement, stopping means for stopping the rotation of the packaging, radiating means for irradiating the packaging, image recording means for making image recordings of at least a part of the content of the packaging, transmission means for transmitting the image recordings from the recording means to image analysis means, image analysis means for analysing image information of the image recordings for the availability of information relating to the presence of undesired particles.

According to a preferred embodiment at least a part of the radiation has a frequency falling within the infrared range. Hereby the above stated advantages can be achieved.

In a preferred embodiment the means for making image recordings comprise at least one camera. The irradiating means further comprise at least one mounting bracket comprising a plurality of radiation sources such as LEDs. For the use of LEDs in the range of the visible light, more specifically light with a wavelength of 590 nanometres, such a mounting bracket is for instance known from the publication of international patent application WO 00/77499.

A preferred embodiment comprises radiating means which are at least partially suitable for emitting radiation with a wavelength falling in the infrared range. An advantage of this embodiment is that specific combinations of radiation with a plurality of wavelengths can be applied which are suitable for specific product-packaging combinations. Using an apparatus as according to this embodiment, such combinations can be readily-defined by experimentation.

In a further preferred embodiment the transmission means comprise means for making use of a communication protocol. A very suitable protocol for this purpose is the so-called FireWire or IEEE 1394. This protocol is for instance suitable since it is for instance intended for end user equipment. The application of different communication protocols, such as for instance Ethernet or a faster version of a similar usable protocol, can however also be seriously envisaged.

It is particularly advantageous if two-way communication is possible between the image recording means and the image analysis means. It hereby becomes possible to make the camera settings, such as for instance diaphragm or sensitivity, adjustable remotely and by means of software.

This is for instance practical for specifically modifying such settings to a bottle-product combination that has to be processed.

In a further preferred embodiment the diameter of the radiating means or the mounting bracket is in the range of 5–11 cm, or even less than 1 cm. As described in the foregoing, this has the advantage that the diameter of the mounting bracket for lighting can be the same size or even smaller that the diameter of the packaging or bottle on which the measurement must be performed.

In a further preferred embodiment the composition of the frequency spectrum of the radiating means is variably adjustable depending on the packaging and/or the product. If radiation sources or LEDs with radiation with a different wavelength are arranged in the mounting bracket, one wavelength or a plurality of wavelengths can be switched on simultaneously. The application of several wavelengths can be optimized for a specific combination of packaging and product.

In a further embodiment a carrousel apparatus comprises a number of measuring apparatuses as described above. The carrousel is provided with first transfer means for transferring packagings from a transport line to the carrousel and second transfer means for transferring packagings from the carrousel to the transport line after performing of the measurements. Advantages of the use of the carrousel are already known. Advantages of the carrousel with measuring apparatus according to the present invention are described in the foregoing, which will be further elucidated hereinbelow.

The carrousel apparatus preferably comprises stationary irradiating means for illuminating packagings in the co-rotatable measuring apparatus as they pass the irradiating means. In the known carrousel and in the carrousel according to the previous embodiment, co-rotating illuminating means are provided for each of the measuring apparatuses for each co-rotating bottle. A plurality of for instance 36 illuminating elements or mounting brackets was hereby required in a specific practical embodiment. In the present invention there are provided for instance twelve mounting brackets or one segment-shaped mounting bracket the size of for instance twelve mounting brackets which only illuminate rotating bottles from the underside during the period of the measurement. This for instance has the advantages that a smaller number of radiation sources is necessary, that the carrousel has a simpler construction and that the power supply for the mounting brackets becomes simpler.

BRIEF DESCRIPTION OF THE DRAWINGS

Further advantages, features and details of the present invention will be elucidated on the basis of the following description of preferred embodiments thereof, with reference to the annexed drawings, in which.

DESCRIPTION OF THE PREFERRED EMBODIMENTS

A beer bottle B (FIG. 1) is clamped in each case between a ring 1 and a head 2 and rotated rapidly and subsequently decelerated by a motor 3, which is coupled to head 2 via a gearing mechanism 4 and a brake 5. Ring 1 and head 2 are therefore mounted rotatably relative to a frame 6. In each case as soon as the bottle is decelerated, light is projected from a light source 7 into the bottle and the movements of possible contaminants in the liquid are transmitted to an image processing station 9 using a CCD-camera 8, wherein they can be made visible on a screen 11 by a processor 10.

Figure 1:
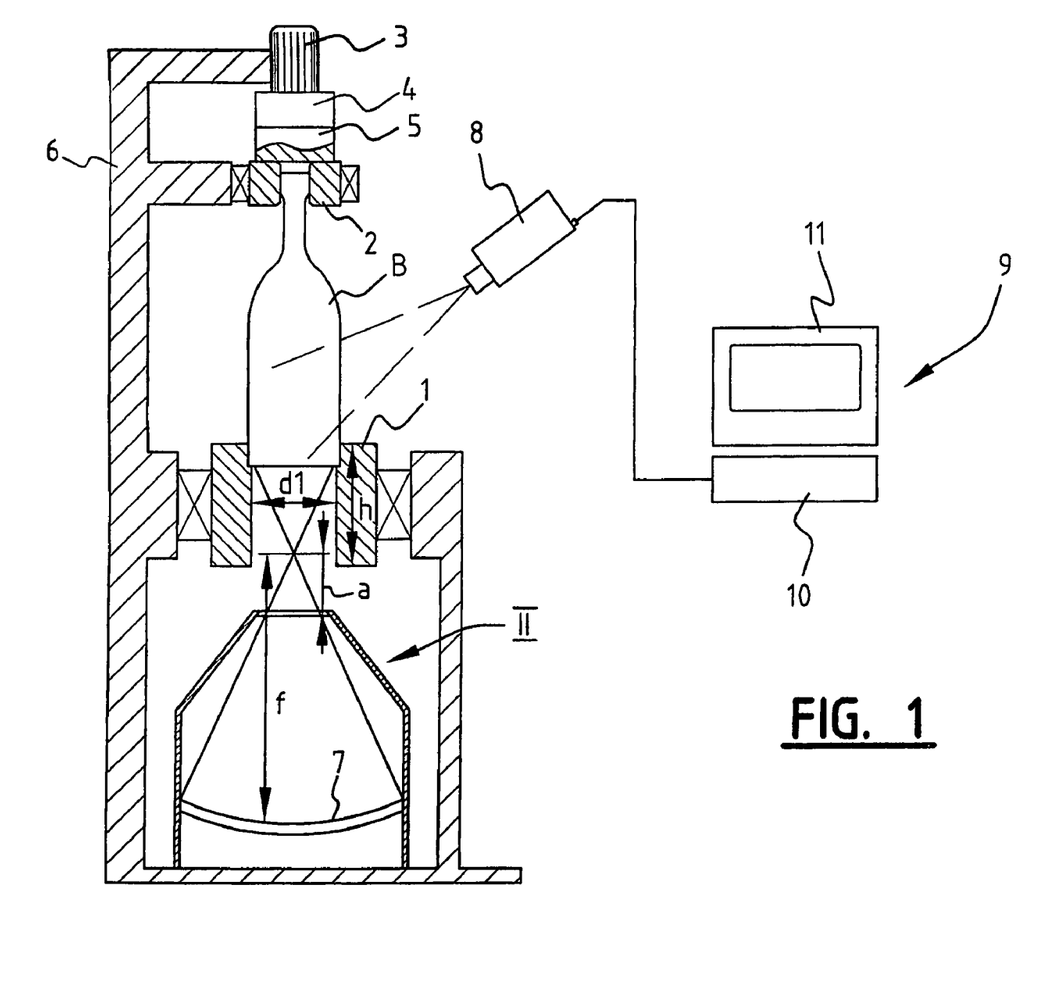
FIG. 1 is a schematic view of a measuring apparatus according to the present invention.

The opening in head 2 has a diameter d1 of 45–50 mm, while the head has a height (h) of about 75 mm. In order to project sufficient light through this opening, the focal point of the beam is situated at a distance a of 25–30 mm relative to a of light source 7. In this preferred embodiment the focal length f amounts to about 185 mm.

The wavelength of infrared light lies in the range between about 600 and 6000 nm. In a preferred embodiment the light sources emit radiation between 700 nm and 1000 nm and preferably between 700 nm and 800 nm.

The mounting bracket can take a very compact form through the use of infrared LEDs. A diameter of 5–11 centimetres hereby becomes possible. This is possible since the intensity of infrared light is greater in this application than the intensity of visible light. The result hereof is that, despite the use of smaller mounting brackets, a sufficient signal is available to detect undesired particles in the product. It is recommended that the diameter of the illuminating means is smaller than the diameter of the largest bottle processed in the carrousel.

In a future preferred embodiment there may even be a single LED with for instance a diameter of 0.5–1 cm (or even smaller), whereby the glass casing can be wholly or partially omitted.

Figure 2:
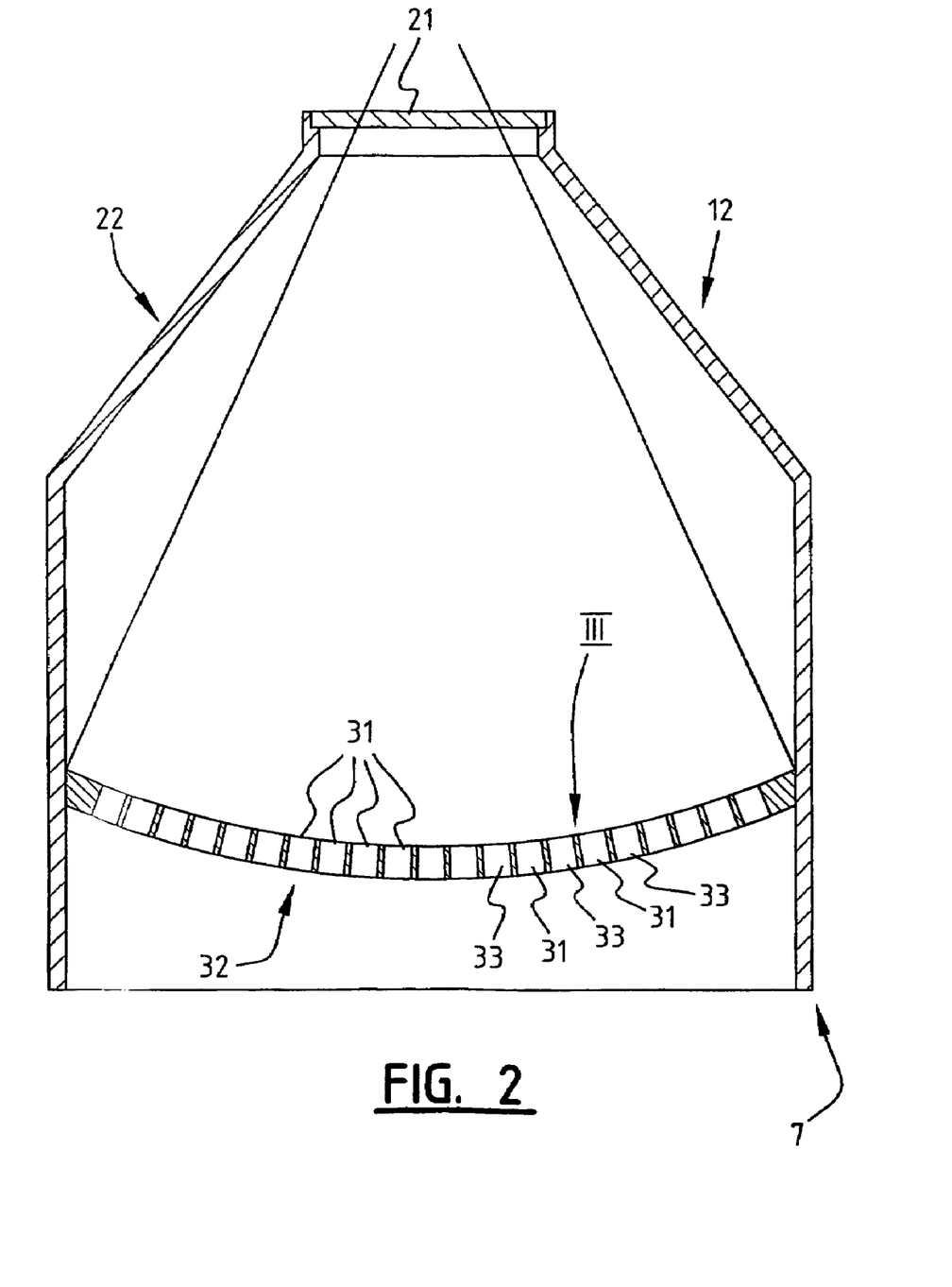
FIG. 2 is a cross-sectional view of detail II of FIG. 1.

Although it is conceivable to have focussing take place with a lens, for instance using a flat Fresnel lens, the light source 7 (FIG. 2) is provided in the present embodiment with a flat window 21 of translucent material, preferably of hard and scratch-resistant material, whereby light source 7 is extremely robust. The casing is further provided with an inclining upper wall 22, whereby moisture and/or dirt in an industrial environment will not adversely affect the intensity of the light source. Because the window is preferably placed in a surface inside the outer edge of the inclining upper wall using a seal (not shown), it can be easily and properly cleaned.

In this preferred embodiment (FIG. 3) a large number of LEDs 31, in the present embodiment about 350, are placed in a spherical holder 32, whereby a focussing action is obtained. The LEDs have a small exit angle in the order of magnitude of 1–6.

As can be further seen (FIG. 2, FIG. 3), different types of LED 31, 33 are applied. These LEDs have a different wavelength. It hereby becomes possible to emit light of two different wavelengths using one mounting bracket. It is possible to apply several different LEDs in one mounting bracket.

In a further embodiment (not shown) the mounting bracket is provided with control means for varying the light intensity of the LEDs. A very light bottle can hereby be irradiated using one mounting bracket. It is also possible for instance to illuminate relatively thick or dark bottles by varying the intensity, in order to ensure an efficient detection. Different types of bottle can hereby be processed very flexibly using a detection apparatus with fixedly mounted brackets. It is further possible to select a suitable intensity-wavelength combination for bottles with particular characteristics, such as bottles with "scuffing", the known "Coca-Cola" bottles with non-homogeneous, light-transmitting capacities, shorter or thicker bottles, bottles with a product containing yeast such as determined types of beer, or bottles decorated by means of for instance a print or a sleeve.

Figure 4:
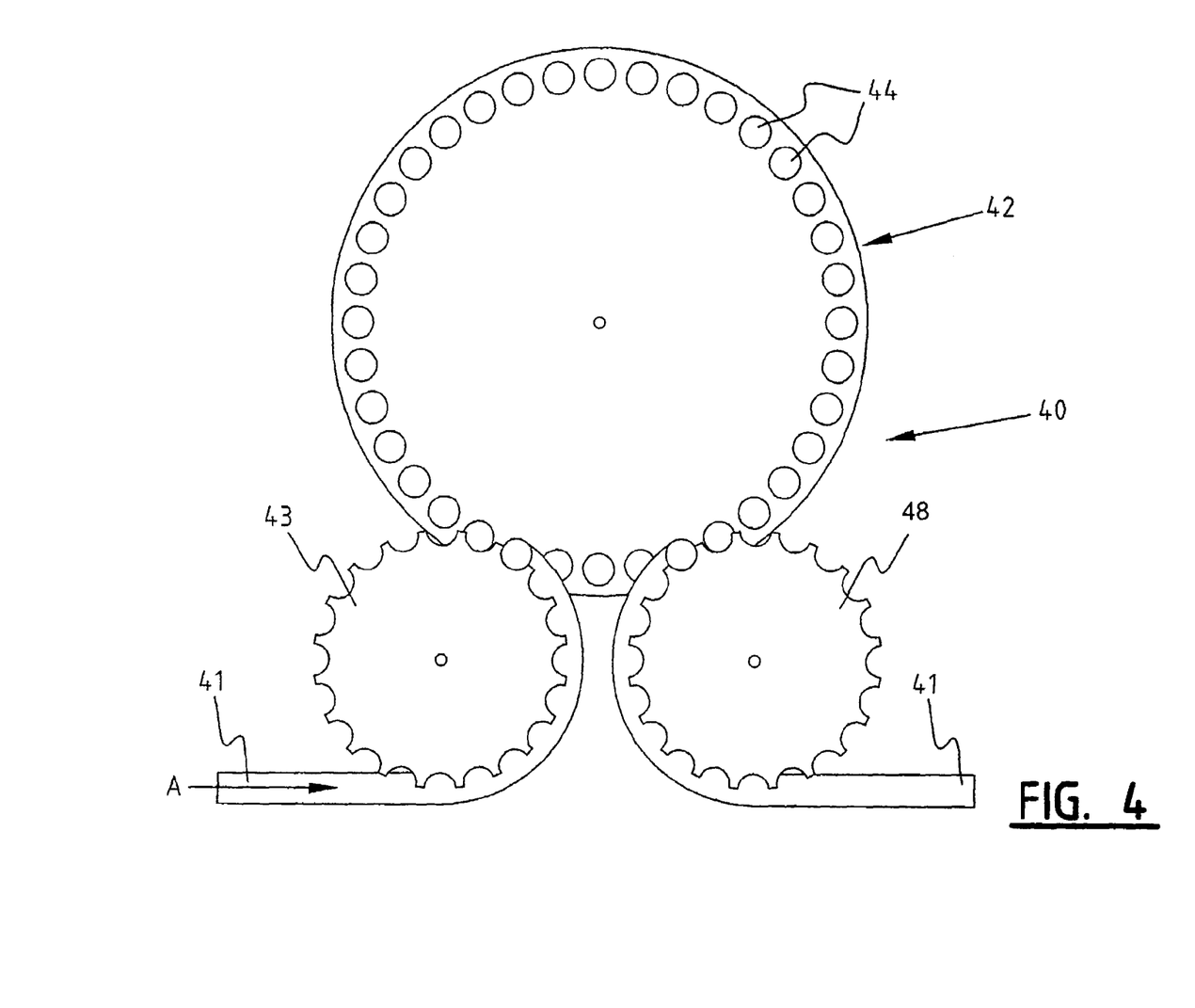
FIG. 4 is a schematic top view of a carrousel measuring system according to an embodiment of the present invention.

A plurality of the detection apparatuses of FIG. 1 is applied in a detection system 40 (FIG. 4) Which is coupled to conveyor belt 41 in which bottles are supplied in the direction of arrow A. In this embodiment carrousel 42 comprises thirty-six detection units 44. In each of the detection units the bottles are rotated, stopped, illuminated and measured as described in the foregoing. For this purpose cameras are arranged at the location of the final twelve positions of carrousel 42 before discharge-transfer unit 48. Once they have been transferred from conveyor belt 41 to carrousel 42 by means of feed-transfer unit 43, bottles can hereby be rotated and stopped and the image recordings can be made before the bottles leave the carrousel again.

Figure 3:
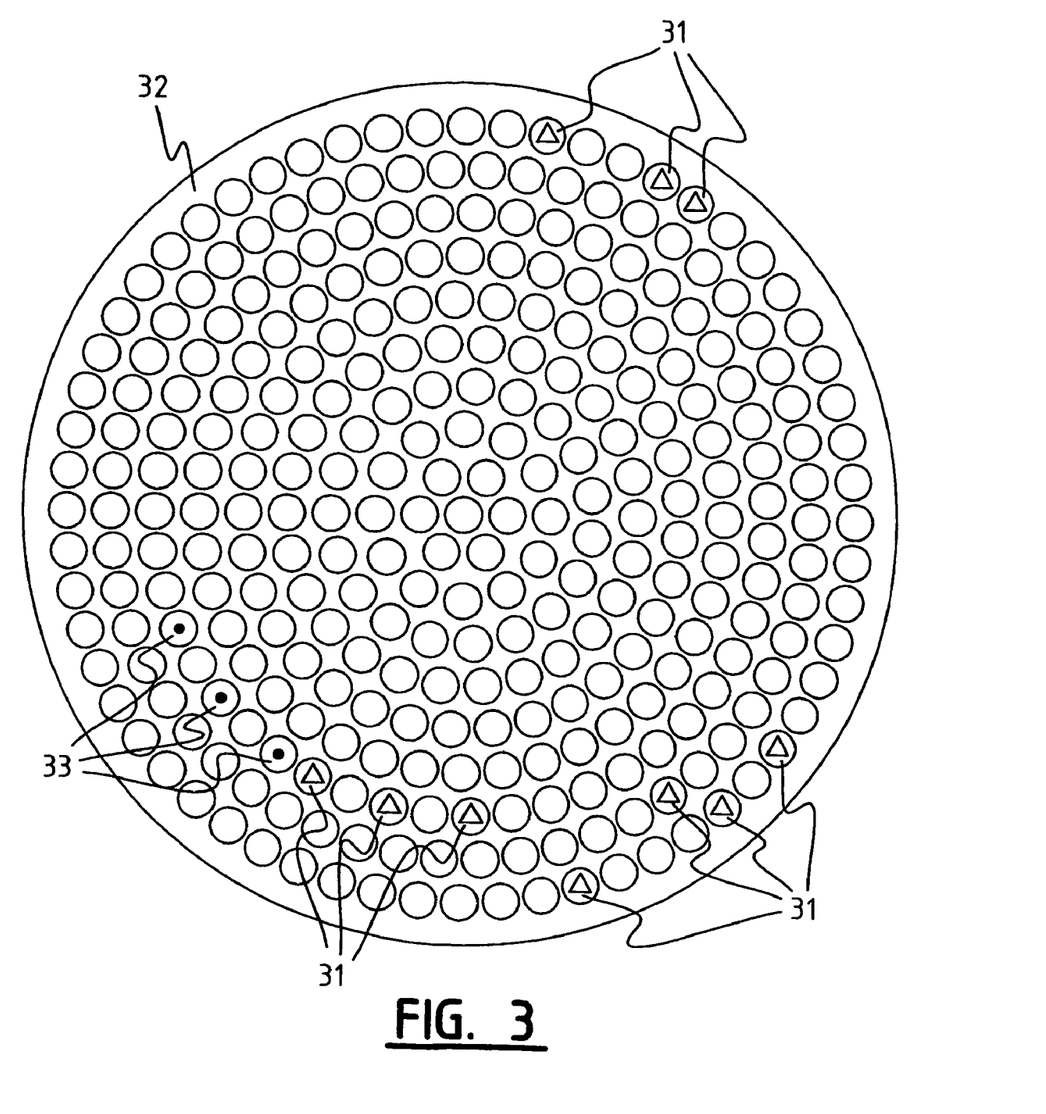
FIG. 3 is a top view of detail III of FIG. 2.
Figure 5:
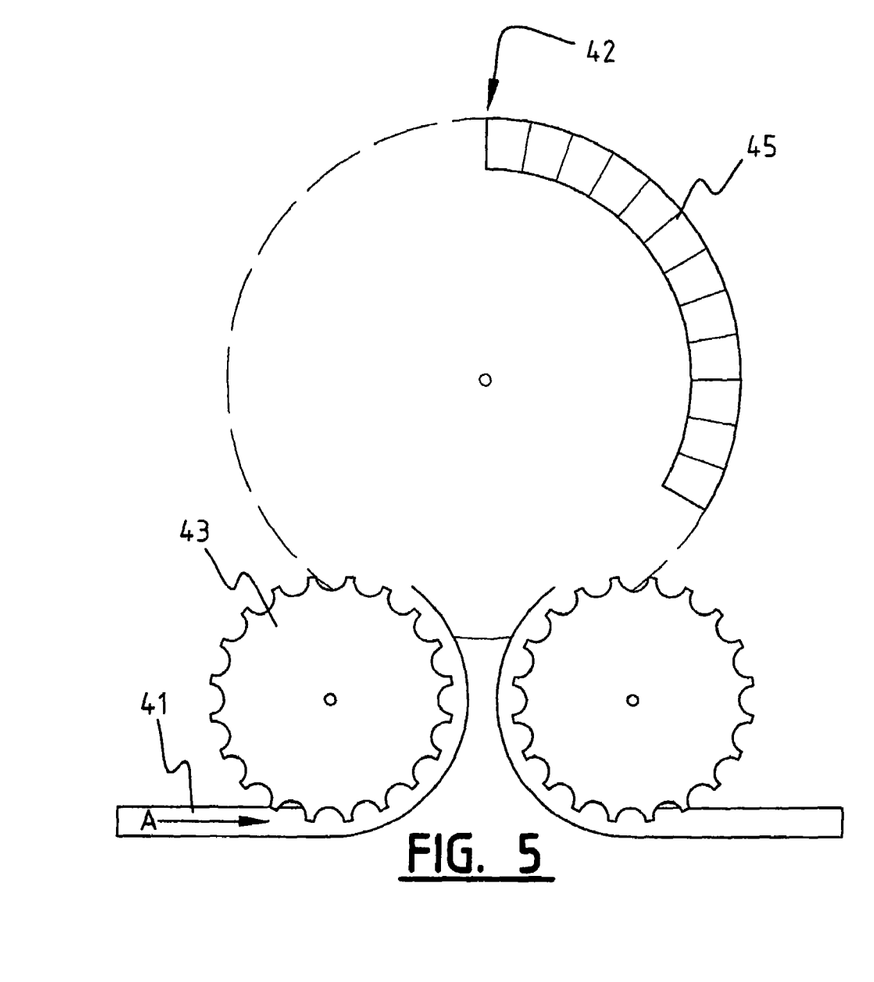
FIG. 5 is a schematic side view of a further embodiment of a carrousel system.
Figure 6:
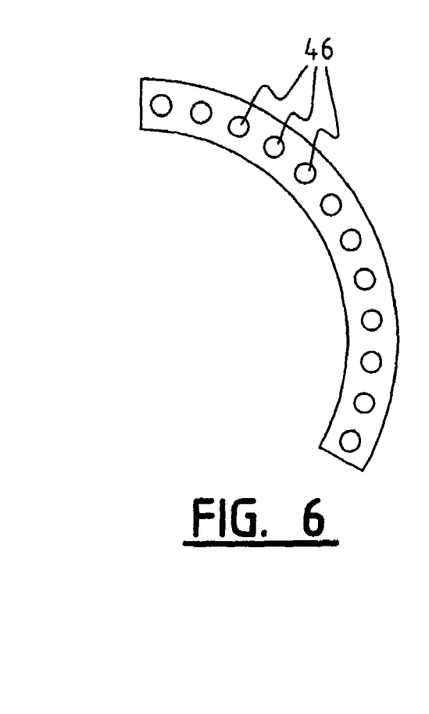
FIG. 6 shows a view of a further embodiment of a detail of the embodiment of FIG. 5.

Carrousel 42 is shown in the embodiment of FIG. 5 without co-rotating mounting brackets for lighting. In this embodiment a segment-shaped mounting bracket 45 is placed on the underside of the carrousel. This mounting bracket illuminates the bottles from the underside, precisely at the part where the cameras for making the image recordings are placed. The advantage of this arrangement is a simpler construction of the carrousel. Segment part 45 can optionally be subdivided into sub-segments, as shown in FIG. 5. An advantage can be that the sub-segments can be controlled independently. Sub-segments can further for instance be replaced independently of each other. Segment part 45 is provided with LEDs (not shown) in similar manner as the mounting bracket of FIG. 3. As seen in the direction of the arc the mounting bracket preferably takes a curved form in similar manner as in FIG. 2, for the purpose of focussing the light in the direction of the bottle moving above the mounting bracket. Such a mounting bracket can likewise be provided with a focussing closure such as closure 21 of FIG. 2. An alternative to segment part 45 is the segment part shown in FIG. 6. Situated herein are mounting brackets 46 which are similar to those of FIG. 3. The advantages of the embodiment of FIG. 3 and FIG. 5 are hereby combined.

According to a further aspect of the present invention, the connection between computer 10 and camera 8 is embodied by means of a connection with a communication protocol. Envisaged here is for instance FireWire or IEEE 1394. An advantage hereof is the fast data transfer made possible by this standard. This protocol can be fitted into the system with relatively simple hardware.

A further application of a system according to the present invention is that the filling level of full bottles can be checked. In transparent bottles the filling level could be detected by means of a detection system on the basis of visible light. An embodiment based on the present invention which makes use of infrared light provides the option of checking the filling level in non-transparent bottles such as printed bottles, or a bottle packed for instance using a sleeve. The filling level of such bottles has been checked according to the prior art using X-radiation. Such a solution is very expensive and, in view of the nature of X-radiation, requires structural and organizational measures which are unnecessary for making use of the present invention.

The above described apparatuses are able to determine very precisely the presence of foreign particles such as glass particles. Particularly in the case of particles of a size which are harmful to health, as defined by institutions such as the FDA in the United States of America and the Health Protection Branch in Canada, these apparatus provide very good results, even in the first trials. The above described fine-adjustment to be established experimentally subject to specific product-packaging combinations can result in improvement within the scope of this invention.

The present invention is not limited to the above described preferred embodiment thereof, the rights sought being rather defined by the following claims, within the scope of which many modifications can be envisaged.

The invention claimed is:

1. An apparatus for performing measurements on packaging containing a liquid product, the packaging having a bottom, the apparatus comprising:
   a rotation device for rotating the packaging for setting the packaging with content into a rotating movement;
   a stopping device operable on the packaging for stopping the rotation of the packaging;
   a radiation emitter for irradiating the packaging;
   an image recorder positioned and operable for making image recordings of at least a part of the content of the packaging;
   transmission elements operable for transmitting the image recordings from the image recorder to an image analyzer;
   an image analyzer operable for analyzing image information of the image recordings for availability of information relating to the presence of undesired particles in the packaging;
   a rotatable carrousel apparatus comprising a plurality of said rotation devices and a plurality of said stopping devices; and
   a mounting bracket for mounting the radiation emitter, the mounting bracket being positioned stationary with respect to the rotatable carrousel apparatus in such a manner that the radiation emitter irradiates the bottom of the packaging.

2. The apparatus as claimed in claim 1, wherein the image analyzer comprises a device for distinguishing between information relating to particles which normally form part of the product and information relating to the undesired particles.

3. The apparatus as claimed in claim 1, wherein the transmission elements are operable to communicate by a communication protocol for selectively transmitting image information and also information for adjusting the image recorder from or via the analyzer.

4. The apparatus as claimed in claim 3, wherein the transmission elements are operable for enabling two-way communication.

5. The apparatus as claimed in claim 1, further comprising an intensity controller operable for variable adjustment of the intensity of the radiation emitter.

6. The apparatus as claimed in claim 5, further comprising a frequency controller operable for constructing the frequency spectrum of the radiation emitter.

7. The apparatus as claimed in claim 1, wherein the radiation emitter is operable for emitting radiation with a wavelength falling within the infrared range.

8. The apparatus as claimed in claim 7, in which the radiation emitter comprises at least one infrared LED operable for emitting infrared radiation.

9. The apparatus as claimed in claim 1, wherein the radiation emitter comprises a plurality of stationary irradiating devices and further comprises a plurality of the mounting brackets.

10. The apparatus as claimed in claim 1, wherein the radiation emitter comprises a plurality of light sources operable to emit radiation of different frequencies.

11. The apparatus claimed in claim 10, in which the radiation emitter comprises at least one infrared LED operable for emitting infrared radiation.

12. The apparatus as claimed in claim 1, wherein the diameter of the radiation emitter or the mounting bracket is of a diameter larger than the diameter of the packaging to be analysed.

13. An apparatus for performing measurements on packaging containing a liquid product, comprising:
   a rotation device for rotating the packaging for setting the packaging with content into a rotating movement;
   a stopping device operable on the packaging for stopping the rotation of the packaging;
   a radiation emitter for irradiating the packaging, the radiation emitter comprising a stationary mounting bracket for the radiation emitter; the diameter of the radiation emitter or of the mounting bracket is smaller than eleven centimeters;
   an image recorder positioned and operable for making image recordings of at least a part of the content of the packaging;
   transmission elements operable for transmitting the image recordings from the image recorder to an image analyzer;
   an image analyzer operable for analyzing image information of the image recordings for availability of information relating to the presence of undesired particles in the packaging; and
   a carrousel apparatus comprising at least the rotation device and the stopping device.

14. The apparatus of claim 13, wherein the radiation emitter is operable to emit radiation with a wavelength in the infrared range.

15. An apparatus for performing measurements on packaging containing a liquid product, comprising;
   a rotation device for rotating the packaging for setting the packaging with content into a rotating movement;
   a stopping device operable on the packaging for stopping the rotation of the packaging;
   a radiation emitter for irradiating the packaging;
   an image recorder positioned and operable for making image recordings of at least a part of the content of the packaging;
   transmission elements operable for transmitting the image recordings from the image recorder to an image analyzer;
   an image analyzer operable for analyzing image information of the image recordings for availability of information relating to the presence of undesired particles in the packaging;
   a rotatable carrousel apparatus comprising a plurality of said rotation devices and a plurality of said stopping devices; and
   a stationary mounting bracket for mounting the radiation emitter, the stationary mounting bracket being positioned stationary with respect to the rotatable carrousel apparatus in such a manner that the radiation emitter irradiates the bottom of the packaging.

16. The apparatus of claim 15, wherein the radiation emitter comprises a plurality of light sources operable to emit light of different wavelength, at least one light source of the plurality of light sources operable to emit radiation with a wavelength in the infrared range.

17. An apparatus for performing measurements on packaging containing a liquid product, comprising;
   a rotation device for rotating the packaging for setting the packaging with content into a rotating movement;
   a stopping device operable on the packaging for stopping the rotation of the packaging;
   a radiation emitter for irradiating the packaging;
   an image recorder positioned and operable for making image recordings of at least a part of the content of the packaging;
   transmission elements operable for transmitting the image recordings from the image recorder to an image analyzer;
   an image analyzer operable for analyzing image information of the image recordings for availability of information relating to the presence of undesired particles in the packaging;
   a rotatable carrousel apparatus comprising a plurality of said rotation devices and a plurality of said stopping devices;
   a mounting bracket for mounting the radiation emitter, the mounting bracket being positioned stationary with respect to the rotatable carrousel apparatus in such a manner that the radiation emitter irradiates the bottom of the packaging; and
   a frequency controller operable for constructing the frequency spectrum of the radiation emitter.

18. The apparatus of claim 17, wherein the radiation emitter comprises a plurality of light sources operable to emit light of different wavelengths, at least one light source of the plurality of light sources operable to emit radiation with a wavelength in the infrared range.

19. An apparatus for performing measurements on packaging containing a liquid product, comprising;
   a rotation device for rotating the packaging for setting the packaging with content into a rotating movement;
   a stopping device operable on the packaging for stopping the rotation of the packaging;
   a radiation emitter for irradiating the packaging, the radiation emitter comprising at least one infrared LED operable for emitting infrared radiation;
   an image recorder positioned and operable for making image recordings of at least a part of the content of the packaging;
   transmission elements operable for transmitting the image recordings from the image recorder to an image analyzer;
   an image analyzer operable for analyzing image information of the image recordings for availability of information relating to the presence of undesired particles in the packaging;
   a rotatable carrousel apparatus comprising a plurality of said rotation devices and a plurality of said stopping devices, and
   a mounting bracket for mounting the radiation emitter, the mounting bracket being positioned stationary with respect to the rotatable carrousel apparatus in such a manner that the radiation emitter irradiates the bottom of the packaging.

* * * * *